United States Patent [19]

Jolson

[11] Patent Number: 4,787,735
[45] Date of Patent: Nov. 29, 1988

[54] NIGHT VISION SYSTEM AND METHOD

[76] Inventor: Consta Jolson, 207 N. Jasper Ave., Margate, N.J. 08402

[21] Appl. No.: 812,756

[22] Filed: Dec. 23, 1985

[51] Int. Cl.⁴ ............................................. A61B 3/10
[52] U.S. Cl. .................................... 351/221; 351/246
[58] Field of Search .............. 351/200, 205, 211, 221, 351/243, 246; 358/161

[56] References Cited

U.S. PATENT DOCUMENTS 3,112,424 11/1963 Suhrmann ........................... 358/161
4,614,411 9/1986 Horenz ................................ 351/221

Primary Examiner—Charles T. Jordan
Assistant Examiner—Michael J. Carone
Attorney, Agent, or Firm—Robert K. Youtie

[57] ABSTRACT

A night vision system in which a lamp radiating toward the pupil of a user has its intensity controlled in response to the sensing of other illumination directed toward the user's pupil, so that pupil size is reduced in the anticipation of an increase in illumination which would otherwise considerably reduce retinal sensitivity.

9 Claims, 2 Drawing Sheets

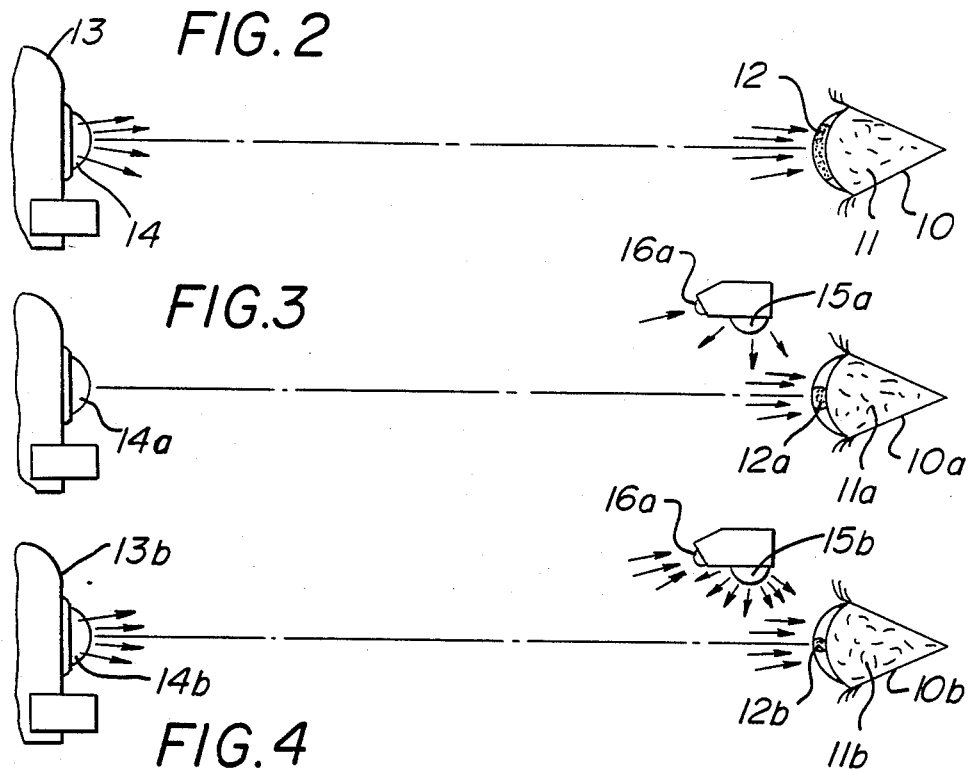
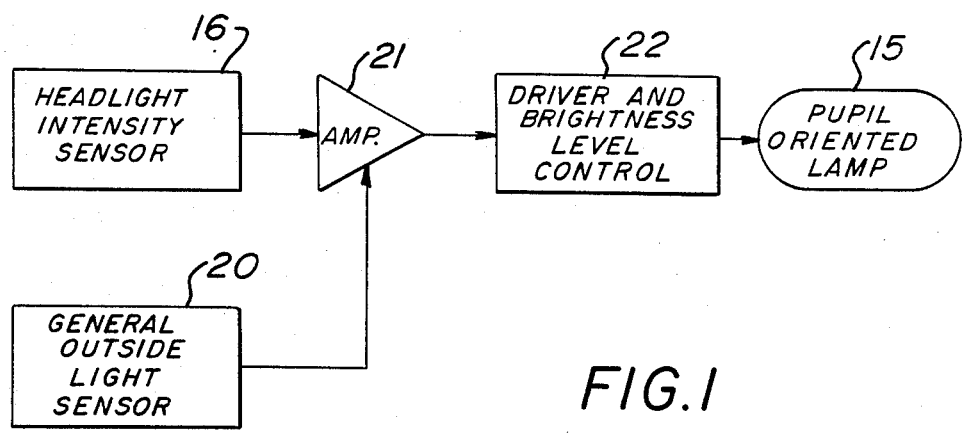

4,787,735

NIGHT VISION SYSTEM AND METHOD

BACKGROUND OF THE INVENTION

As is well known to those experienced in night driving, and other night vision activities, the pupil is normally enlarged under conditions of low illumination to gather a maximum of light; and, upon the entry of relatively high intensity light through a dilated pupil there is dangerous loss of retinal sensitivity and resulting night blindness. While there have been proposed a variety of devices for overcoming this night blindness, such as screens, shutters, and the like, these prior devices have not been found satisfactory, and the problem persists.

While the method and apparatus of the present invention have been primarily developed and employed for use in vehicle operation, and will be illustrated and described hereinafter with particular reference thereto, it is appreciated that the instant invention is capable of many varied applications, all of which are intended to be comprehended herein.

SUMMARY OF THE INVENTION

It is an important object of the present invention to provide a method and apparatus for improving night vision under conditions of intermittent extreme brightness in the field of view, such as the glare of an oncoming automotive headlight on a narrow road.

It is a more particular object of the present invention to provide a method and apparatus of the type described wherein the user's pupil size is reduced prior to full brightness of an oncoming headlamp so that retinal sensitivity loss is limited and night blindness is minimized or obviated.

It is a further object of the present invention to provide a method and apparatus having the advantageous characteristics mentioned in the preceding paragraph which is adjustable for adaptation to persons having different visual ability.

It is a further object of the present invention to provide a method and apparatus for enhancing night vision which may accomodate to environmental light conditions, as well as intermittent extreme brightness or glare.

Other objects of the present invention will become apparent upon reading the following specification and referring to the accompanying drawings, which form a material part of this disclsoure.

The invention accordingly consists in the features of construction, combinations and arrangements of parts and method steps, which will be exemplified in the following description, and of which the scope will be indicated by the appended claims.

BRIEF DESCRIPTION OF THE DRAWINGS

FIG. 1 is a block diagram showing apparatus of the present invention.

FIG. 2 is a diagrammatic representation of the prior art illustrating the pupil condition in night driving under intermittent brightness.

FIG. 3 is a similar diagrammatic representation showing the pupil during night driving with the method and apparatus of the present invention, in the absence of high intensity or bright illumination.

FIG. 4 is a similar diagrammatic representation showing the instant invention under conditions of high intensity or bright illumination during night driving.

DESCRIPTION OF THE PREFERRED EMBODIMENT

Figure 5:
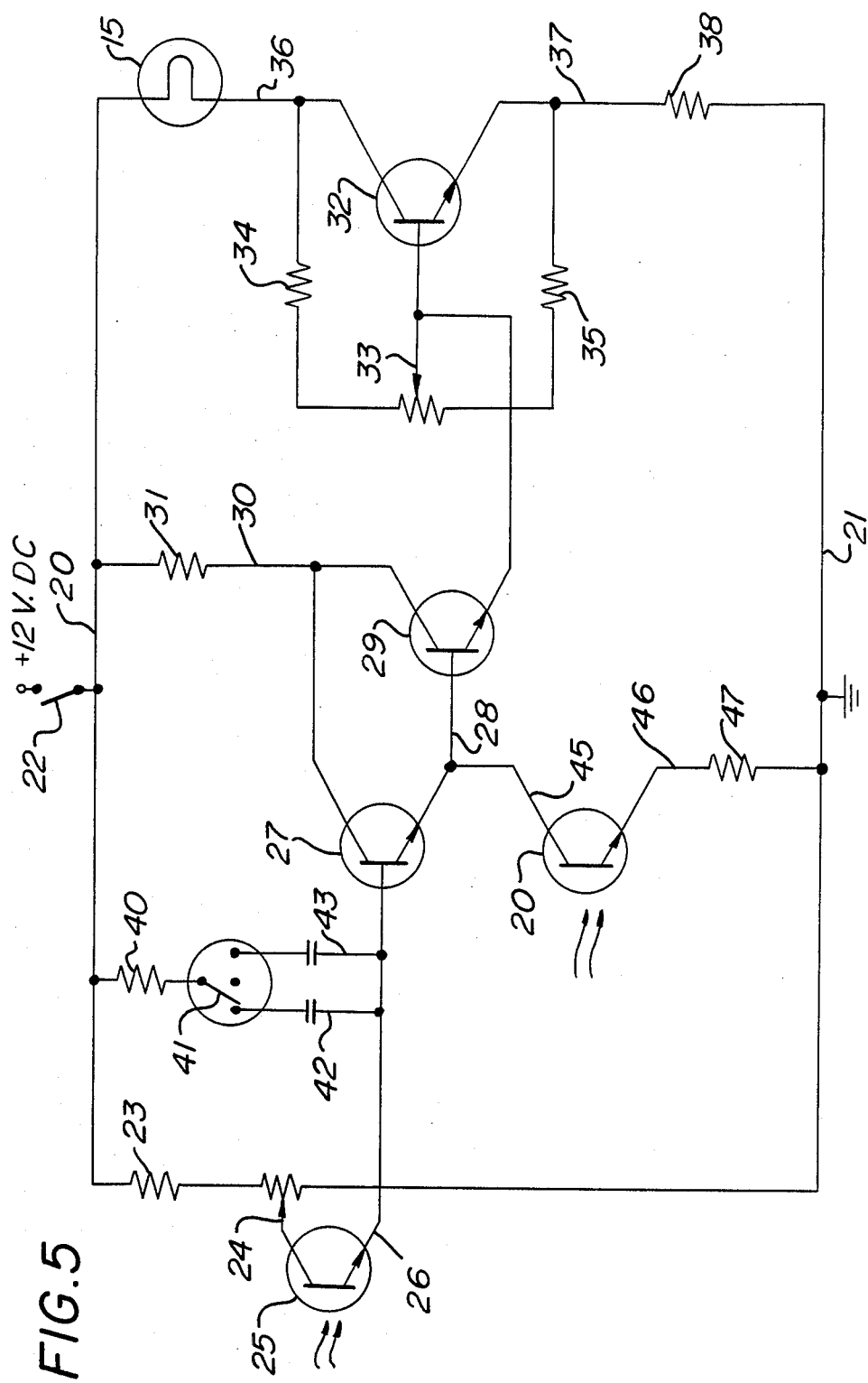
FIG. 5 is a schematic illustrating the apparatus of the present invention.

Referring now more particularly to the drawings, and specifically to FIG. 2 thereof, a user's eye is there generally designated 10, and includes an iris 11 having a central opening or pupil 12. The eye 10 may be assumed to be that of an automobile driver, under conventional night driving conditions, where the pupil is highly dilated to gather a maximum of light. In the path of vision, and substantially directly ahead of the user's eye 10 may be an oncoming vehicle 13 having headlights 14 radiating high intensity light toward the eye 10. Headlamps 14 do not cause appreciable discomfort or loss of retinal sensitivity until relatively close to the driver's eye 10. However, as soon as the headlight reaches a critical distance from the eye 10, the high headlight intensity is directed through the highly dilated pupil 12 to cause substantial loss of retinal sensitivity and substantially instantaneous night blindness. Visual acuity may be considerably reduced or lost throughout substantially the entire field of view until the headlights 14 pass, and for a short time thereafter. That is, even reduction of intensity by removal of the headlights 14 does not immediately cure the night blindness, but the retina requires a recovery period.

Considering FIG. 3, the operator's eye 10a has the pupil 12a only moderately dilated under the night driving condition absent illumination from oncoming headlights 14a. The pupil 12a is moderately dilated, or closed relative to the pupil 12 by reason of a pupil oriented lamp 15a mounted in the vehicle of the user for directing its radiation to the user's pupil. That is, the pupil oriented lamp 15a radiates toward the pupil 12a to moderately dilate the pupil, even under conditions of extreme external darkness. A light sensor 16a is directed forwardly, along the path of movement of the user's vehicle, to receive illumination from oncoming vehicle headlights. The sensor 16a is thus directional, and connected, as will appear more fully hereinafter, to the lamp 15a for controlling the intensity of the latter.

This is seen diagrammatically in FIG. 4. The eye 10b is shown with the iris 11b substantially closed to reduce or minimize the pupil opening 12b. This, in accordance with the teachings of the present invention, is in response to oncoming illumination by headlamps 14b of an approaching vehicle 13b.

More specifically, the pupil oriented lamp 15b is radiating a relatively high intensity illumination toward the eye 10b, in response to radiation received from the headlamps 14b by the sensor 16b. The sensor 16b is responsive to incipient radiation from the headlamps 14b at a considerable distance away from the user's eye 10b, to begin gradually increasing the intensity of the lamp 15b well before headlamps 14b reach that critical distance from the eye 10b at which the headlamp illumination may cause night blindness. Thus, well before the headlamps 14b can become a problem to the eye 10b, the pupil 12b has started closing as a result of illumination from lamp 15b. When the headlamps 14b reach that critical distance, the pupil 12b is sufficiently closed so that excessive brightness is not a problem to the eye 10b.

In practice, radiation from the lamp 15b is advantageously selected from the green to violet part of the spectrum, so as to minimize interference with visual acuity of the user. The filter color and resultant illumination wave length may be selected as desired by the user, violet giving a minimal visual response.

The sensor 16a and lamp 15b may be mounted on the dashboard or windshield of a motor vehicle, say on the left hand side of a left hand drive car, and may occupy relatively little space so as not to affect the driver's field of view.

With conventional sensor means, such as phototransistors, photoresistors, photodiodes, or photocells, oncoming light can be sensed at a distance of up to ½ mile, well before adversely affecting the driver's eyes. The light source or pupil lamp 15b may be of any desired type, including filamentary, light emitting diodes, or other.

In the block diagram of FIG. 1, the sensor is generally designated 16, and would be mounted on the vehicle, as on the dashboard, or other suitably convenient location. The sensor 16 is directional for response to illumination in the path of the driver's vision. An additional sensor 20 may be suitably located for sensing illumination in the general environment, outside the path directly ahead of the user. Thus, the auxiliary sensor 20 serves to sense ambient lighting conditions, for a purpose appearing presently. Both the primary sensor 16 and auxiliary sensor 20 feed signals to amplifier means 21, which in turn controls an output driver 22. The driver 22 operates a pupil directed lamp 15 for varying the intensity, in accordance with the instant invention.

More specifically, a schematic diagram is shown in FIG. 5 as one operative embodiment of the instant invention, while it is appreciated that many variations may be employed without departing from the intent of the instant invention.

A source of voltage supply is connected between conductors 20 and 21, being respectively located at +12 volts and ground. An on-off switch 22 connects the conductor 20 to a voltage supply.

Connected in series with each other and across the supply voltage is a current limiting resistor 23, and a potentiometer 24. A light responsive device or sensor, say in the form of a phototransistor 25 has its collector connected to the voltage divider 24. Thus, current to the phototransistor 25 is limited by resistor 23 and adjusted by potentiometer 24.

Photocurrent generated by the sensor 25 is applied by way of the emitter through conductor 26 to the base of NPN transistor 27. The emitter of transistor 27 is, in turn, connected by conductor 28 to the base of transistor 29, both transistors 27 and 29 having their collectors biased from conductor 20 through conductor 30, which may include a voltage dropping resistor 31. The transistors 27 and 29 may constitute stages of a Darlington current amplifier.

An additional transistor 32 has it base connected to the emitter of transistor 29, the base being biased by connection to a potentiometer 33 in series with resistors 34 and 35. The final stage amplifier 32 serves as an output driver, its collector being connected by conductor 36 through lamp 15 to supply line 20, and the emitter of transistor 32 being connected by conductor 37 through current limiting resistor 38 to the ground line 21.

Thus, it will be apparent that a photocurrent generated by transistor 25 responsive to receiving illumination from oncoming headlights is amplified by transistors 27 and 29, the output of which upsets the bias of driver transistor 32 to drive the lamp 15 in an analog manner.

In addition, a resistance capacitance circuit is connected between the conductors 20 and 26, a resistor 40 being connected from conductor 20 to an on-off-on selector switch 41. The switch 41 is selectively connectible to either of capacitor 42, off position, or capacitor 43, for connection therethrough to conductor 26.

The resistance capacitance network 40–43, in accordance with its selected time constant, discharges after the photosensor 25 is actuated to produce after-glowing effect to the lamp 15. That is, the lamp 15 gradually diminishes its intensity of illumination in a lagging relationship with respect to reduction of the illumination of the oncoming headlights, so that reduction in intensity of the pupil oriented lamp is gradual, rather than immediate. The degree of lag is selected by the switch 41 being connected to one or the other of condensors 42 and 43, one being larger than the other.

Further, the auxiliary sensor 20 may be provided by a transistor having its collector connected by conductor 45 to conductor 28, and having its emitter connected by conductor 46 through current limiting resistor 47 to ground. The transistor 20 is photosensitive and directed to sense a general level of surrounding illumination, which signal is fed to amplifier stage 29 and output driver 32 to decrease the photocurrent in case of daylight or intensive road illumination which controls lamp 15.

Thus, the potentiometer 24 may be adjusted to control the intensity of illumination by lamp 15 in the presence of sensed illumination along the path of vehicle movement, while potentiometer 33 controls the intensity level of the lamp in the absence of external actuating illumination.

From the foregoing, it is seen that the method and apparatus of the present invention are well adapted to accomplish their intended objects in a simple, efficient and reliable manner.

Although the present invention has been described in some detail by way of illustration and example for purposes of clarity of understanding, it is understood that certain changes and modifications may be made within the spirit of the invention.

What is claimed is:

1. A night vision system comprising a pupil oriented lamp for direction toward a user's eye, sensor means for sensing additional illumination directed toward the pupil, and control means operatively connected between said sensor means and pupil oriented lamp for varying the intensity of the latter responsive to additional illumination sensed, to contract the pupil for receiving radiation from said additional illumination without dangerous loss of retinal sensitivity and, said sensor means comprising directional photo-sensitive means for only sensing additional illumination in a path directly ahead of a user.

2. A night vision system according to claim 1, said control means being responsive to the incipient additional light for gradually increasing the intensity of said pupil oriented lamp to comfortably contract the pupil in preparation for receiving said additional illumination.

3. A night vision system according to claim 1, said sensing means also comprising nondirectional photosensitive means for sensing additional illumination out of said path.

4. A night vision system according to claim 3, said control means being responsive to increase and decrease of said additional illumination out of said path to, respectively, decrease and increase the intensity of said pupil oriented lamp.

5. A night vision system according to claim 4, said control means comprising amplifier means for increasing the intensity of said pupil oriented lamp at a greater amplification for said additional illumination in said path than out of said path.

6. In the method of enhancing night vision, the steps comprising: directing a pupil lamp toward the user's eye to moderate dilation of the pupil, sensing oncoming illumination in the path directly ahead of the user, and increasing the intensity of the pupil lamp responsive to sensed oncoming illumination, to contract the pupil for more comfortably receiving radiation from said oncoming illumination.

7. The method according to claim 6, further characterized in increasing the intensity of the pupil lamp in amplified relation with respect to the oncoming illumination, to contract the pupil in anticipation of the oncoming illumination.

8. The method according to claim 6, in combination with sensing additional illumination out of said path, and reducing the intensity of said pupil lamp responsive to sensed additional illumination out of the path.

9. The method according to claim 6, in combination with gradually reducing the intensity of the pupil lamp in a lagging relation with respect to reduced intensity of the additional illumination.

* * * * *